(12) United States Patent
Lagow

(10) Patent No.: US 7,045,105 B2
(45) Date of Patent: May 16, 2006

(54) CALCIUM PHOSPHATE BONE REPLACEMENT MATERIALS AND METHODS OF USE THEREOF

(76) Inventor: Richard J. Lagow, 6204 Shadow Mountain Dr., Austin, TX (US) 78731

( * ) Notice: Subject to any disclaimer, the term of this patent is extended or adjusted under 35 U.S.C. 154(b) by 231 days.

(21) Appl. No.: 10/327,344

(22) Filed: Dec. 20, 2002

(65) Prior Publication Data

US 2004/0022825 A1 Feb. 5, 2004

Related U.S. Application Data

(60) Provisional application No. 60/342,622, filed on Dec. 21, 2001.

(51) Int. Cl.
*C01B 25/32* (2006.01)
*C04B 38/02* (2006.01)
*A61F 2/28* (2006.01)

(52) U.S. Cl. .................. 423/305; 423/308; 423/309; 423/311; 501/84; 623/16.11; 623/23.56

(58) Field of Classification Search .............. 423/308, 423/309, 311, 305; 623/16.11, 23.56; 501/84
See application file for complete search history.

(56) References Cited

U.S. PATENT DOCUMENTS

| | | | | |
|---|---|---|---|---|
| 3,929,971 A | * | 12/1975 | Roy | 423/308 |
| 4,195,366 A | * | 4/1980 | Jarcho et al. | 623/23.56 |
| 4,497,075 A | * | 2/1985 | Niwa et al. | 424/423 |
| 4,503,157 A | * | 3/1985 | Hatahira | 501/1 |
| 4,752,457 A | * | 6/1988 | Toriyama et al. | 423/308 |
| 4,952,323 A | * | 8/1990 | Nakabayashi et al. | 210/691 |
| 5,158,756 A | * | 10/1992 | Ogawa et al. | 423/309 |
| 5,264,215 A | | 11/1993 | Nakabayashi et al. | 424/423 |
| 5,650,176 A | * | 7/1997 | Lee et al. | 424/602 |
| 5,783,217 A | * | 7/1998 | Lee et al. | 424/602 |
| 5,858,318 A | * | 1/1999 | Luo | 423/308 |
| 5,997,624 A | * | 12/1999 | Chow et al. | 106/35 |
| 6,002,065 A | * | 12/1999 | Constantz et al. | 423/308 |
| 6,037,519 A | * | 3/2000 | McKay | 423/305 |
| 6,210,715 B1 | * | 4/2001 | Starling et al. | 424/489 |
| 6,231,607 B1 | | 5/2001 | Ben-Bassat et al. | 623/16.11 |
| 6,287,341 B1 | | 9/2001 | Lee et al. | 623/16.11 |
| 6,306,297 B1 | * | 10/2001 | Ichitsuka et al. | 210/198.2 |

FOREIGN PATENT DOCUMENTS

GB 2078696 1/1982

OTHER PUBLICATIONS

Chow et al. "Self-setting calcium phosphate cements." *Mater Res. Soc. Symp. Proc.* 1993;179:3-24, (no month).
Cornell "Initial clinical experience with use of Collagraft™ as a bone graft substitute." *Tech. Orthop.* 1992;7:55-63, (no month).
Feenstra et al. "Medical use of calcium phosphate ceramics." In *Bioceramics of Calcium Phosphate*, CRC Press, 1983; 131-141, (no month).

(Continued)

*Primary Examiner*—Wayne A. Langel
(74) *Attorney, Agent, or Firm*—Lahive & Cockfield, LLP; Giulio A. DeConti, Jr.; Cynthia M. Soroos

(57) ABSTRACT

Methods of making porous calcium phosphate bone replacement materials are discussed.

17 Claims, 5 Drawing Sheets

OTHER PUBLICATIONS

Feldman et al. "Factors affecting soft tissue ingrowth into porous implants." Transactions 2nd World Congress Biomaterials Society, 10th Annual Meeting, 1984;37, (no month).

Lagow et al. "High-performance pure calcium phosphate bioceramics: The first weight bearing, completely resorbable synthetic bone replacement materials." *Progress in Inorganic Chemistry* Karlin ed., 2001; 50:317-342, (no month).

Levin et al. "A comparison of iliac marrow and biodegradable ceramic in periodontal defects." *J. Biomed. Mater. Res.* Mar. 1975;9(2):183-95.

Nery et al. "Bioceramic implants in surgically produced infrabony defects." *J. Periodontol.* Jun. 1975;46(6):328-47.

* cited by examiner 26.4X 50.5X 26.4X

CALCIUM PHOSPHATE BONE REPLACEMENT MATERIALS AND METHODS OF USE THEREOF

RELATED APPLICATIONS

This application claims priority to U.S. Provisional Application Serial No.: 60/342,622, filed Dec. 21, 2001, entitled "Calcium Phosphate Bone Replacement Materials and Methods of Use Thereof." The entire contents of the aforementioned application are hereby incorporated herein by reference in its entirety.

BACKGROUND

Trauma, pathological degeneration, or congenital deformity may result in the need for surgical reconstruction or replacement of bone tissue. Reconstructive surgery is based upon the principle of replacing defective bone tissue with viable, functioning alternatives. In skeletal applications, surgeons have historically used bone grafts. The two main types of bone grafts currently used are autografts and allografts. An autograft is a section of bone taken from the patient's own body, while an allograft is taken from a cadaver. This method of grafting provides the defect site with structural stability and natural osteogenic behavior. However, both types of grafts are limited by certain uncontrollable factors. For autografts, the key limitation is donor site morbidity where the remaining tissue at the harvest site is damaged by removal of the graft. Other considerations include the limited amount of bone available for harvesting, and unpredictable resorption characteristics of the graft. The main limitation of allografts has been the immunologic response to the foreign tissue of the graft. The tissue is often rejected by the body and is subject to the inflammatory response. Allografts are also capable of transmitting disease. Although a thorough screening process eliminates most of the disease carrying tissue, this method is not 100% effective.

Conventional orthopedic implants such as screws, plates, pins and rods serve as loadbearing replacements for damaged bone and are usually composed of a metal or alloy. Although these implants are capable of providing rigid fixation and stabilization of the bone, they cause improper bone remodeling of the implant site due to the large difference in the modulus between bone and metal.

These limitations have initiated the search for a dependable synthetic bone graft substitute. However, in order for an implant to be used as a replacement for bone, it must be capable of both osteointegration and osteoconduction. Osteointegration refers to direct chemical bonding of a biomaterial to the surface of bone without an intervening layer of fibrous tissue. This bonding is referred to as the implant-bone interface. A primary problem with skeletal implants is mobility. Motion of the implant not only limits its function, but also predisposes the implant site to infection and bone resorption. With a strong implant-bone interface, however, mobility is eliminated, thus allowing for proper healing to occur. Osteoconduction refers to the ability of a biomaterial to sustain cell growth and proliferation over its surface while maintaining the cellular phenotype. For osteoblasts, the phenotype includes mineralization, collagen production, and protein synthesis. Normal osteoblast function is particularly important for porous implants that require bone ingrowth for proper strength and adequate surface area for bone bonding.

Calcium phosphate-based materials have been investigated for use as bone replacement materials. Most calcium phosphate biomaterials are polycrystalline ceramics characterized by a high biocompatibility, the ability to undergo osteointegration, and varying degrees of resorbability. Implants made from these materials can be in either a porous or non-porous form. Examples of commercially available calcium phosphate materials include Interpore 200 and Interpore 500. Surgical models using previously developed porous calcium phosphate-based implant materials, however, have shown that porous implants heal more slowly than both autografts and empty defects (Nery et al. *J. Periodotol.* 1975 46:328; Levin et al. *J. Biomed. Mat. Res.* 1975 9:183). Studies on tissue ingrowth in non-resorbable implants have also shown that failure of tissue to completely fill the implant can lead to infection (Feenstra, L. and De Groot, K. "Medical use of calcium phosphate ceramics" In Bioceramics of Calcium Phosphate, De Groot, K. Ed., CRC Press, Boca Raton, Fla., 1983, pp 131–141; Feldman, D. and Esteridge, T. Transactions 2nd World Congress Biomaterials Society, 10th Annual Meeting, 1984, p 37).

Implants synthesized from the calcium phosphate-based material, hydroxyapatite (HA), the major mineral constituent of bone, are commercially available in a porous and non-porous form. Synthetic HA implants have excellent biocompatibility. Blocks of dense HA are not useful in reconstructive surgery because they are difficult to shape and do not permit tissue ingrowth. However, in a non-porous, particulate form, HA has been used successfully in both composite (Collagraft) and cement (Hapset) forms (Chow et al. *Mater. Res. Soc. Symp. Proc.* 1993 179:3–24; Cornell, C. N. *Tech. Orthop.* 1992 7:55). Due to its fragility and lack of compliance, porous HA have been largely limited to dental and maxillofacial surgery.

SUMMARY OF THE INVENTION

In one embodiment, the invention pertains, at least in part, to a method of producing a porous calcium phosphate material. The method includes forming a mixture of calcium ions and phosphate ions having a calcium to phosphorus ratio of 0.1 to 1.67, heating the mixture to an appropriate reaction temperature, and cooling the reaction mixture.

In another embodiment, the invention pertains, at least in part, to a method of producing a porous calcium phosphate material. The method includes forming a mixture of calcium ions and phosphate ions, having a calcium to phosphorus ratio of 0.1 to 1.67, adding a gas-generating material to the mixture, heating said mixture an appropriate temperature, and cooling the mixture. Preferably, the porous calcium phosphate material produced has interconnected pores.

In another embodiment, the invention also pertains to another method of producing a porous calcium phosphate material. The method includes mixing a gas-generating material and a calcium phosphate ceramic precursor, heating the mixture to below the sintering temperature to generate a gas, and sintering the calcium phosphate ceramic precursors to make solid ceramic materials.

In another embodiment, the invention pertains to yet another method of producing a calcium phosphate material. This method includes 1 sublimating a solid chemical in a reactive calcium phosphate mixture or calcium phosphate ceramic precursor, and before undergoing the chemical reaction or sintering the calcium phosphate ceramic precursor.

The invention also pertains, at least in part, to surgical implants which contain a calcium phosphate material produced by the methods of the invention.

In another, embodiment, the invention also pertains to synthetic calcium phosphate material produced by the methods of the invention. In a further embodiment, the calcium phosphate material generated by the methods of the invention is biodegradable.

In a further embodiment, the invention also pertains to a method of treating of bone disorder in a subject. The method includes applying a calcium phosphate material of the invention to a bone of said subject, such that the bone disorder of said subject is treated.

In another embodiment, the invention also pertains to a calcium phosphate material, comprising the calcium salt of:

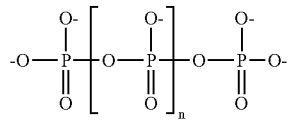

wherein n is an integer between 10 and 1,000,000.

DETAILED DESCRIPTION OF THE INVENTION

Figure 1A:
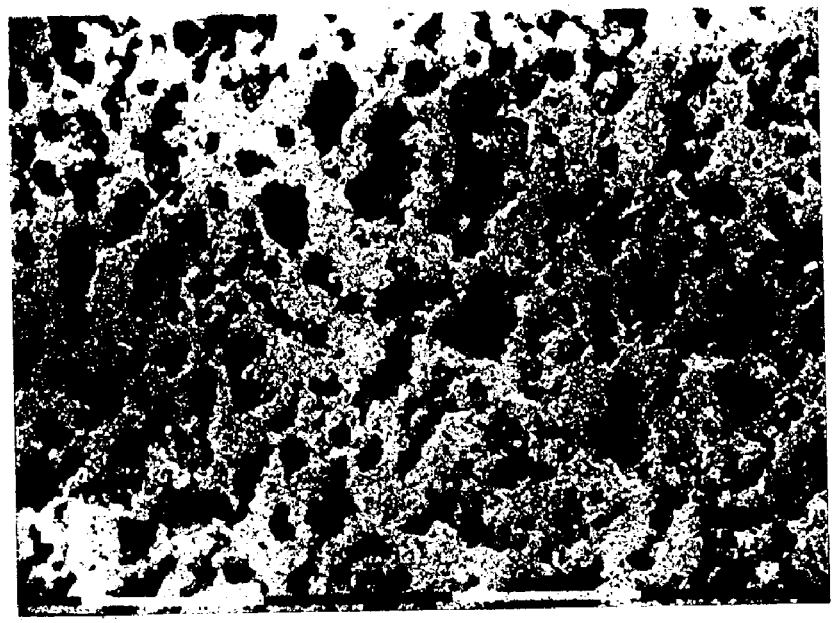
FIG. 1a is a SEM image of the control calcium phosphate material at 26.4 magnification.

A new synthetic calcium phosphate material has been developed. The size, shape and porosity can be both predetermined and controlled in the synthetic process. Pore size and density are important in promoting tissue ingrowth. Both the nonporous and porous materials demonstrate high flexural and compressive strength compared to the other available ceramics and are comparable to autologous bone. This material is a pure calcium phosphate devoid of contaminants such as silicates, zinc and alumina which may possibly retard osteogenesis.

In one embodiment, the invention pertains to a method of producing calcium phosphate material. The method includes forming a mixture of calcium ions and phosphate ions having a calcium to phosphorus ratio of 0.1 to 1.67, heating the mixture to an appropriate reaction temperature; and cooling the reaction mixture. The ratio of calcium to phosphate ions is preferably selected such that the resulting material is able to perform its intended function. For convenience, the calcium to phosphate ion ratio is abbreviated as the "Ca/P ratio."

The term "calcium phosphate material" includes synthetic material comprised of calcium and phosphate ions and, advantageously, non-apatitic. Preferably, the material is synthesized by the methods of the invention and is suitable for its intended purpose, e.g., as a bone replacement. The calcium phosphate material of the invention, advantageously, is porous. The pores may or may not be interconnected.

In a further embodiment, the Ca/P ration is about 0.20 to about 0.80, about 0.25 to about 0.75, about 0.30 to about 0.70, about 0.35 to about 0.65, about 0.40 to about 0.60, about 0.40 to about 0.55, about 0.45 to about 0.50, about 0.46 to about 0.50, about 0.47 to about 0.50, about 0.475 to about 0.495, about 0.480 to about 0.490, or about 0.486. Advantageously the Ca/P ratio is selected on the basis of advantageous biocompatibility and strength.

The calcium ions may be obtained from any source known in the art. Examples of sources of calcium ions that may be used include apatitic calcium phosphates, non-apatitic calcium phosphates, calcium hydroxide, calcium oxide, calcium carbonate, calcium salts, calcium halide, calcium metal, and combinations thereof. In certain embodiments, the calcium ion source is hydroxyapatite.

The phosphate ions may also be obtained from any source known in the art. Examples of sources of phosphate ions include, but are not limited to, orthophosphoric acid, pyrophosphoric acids, condensed phosphates, phosphate of nonmetal cations, metal phosphates, and combinations thereof. In certain embodiments, the phosphate ion source is orthophosphoric acid.

In an embodiment, the invention pertains to a calcium phosphate material of the invention having a 0.486 Ca/P ratio, synthesized from hydroxyapatite and orthophosphoric acid.

The calcium phosphate material is, generally, a highly porous material with average pore sized ranging from, for example, about 5 μm to about 1000 μm or greater. In an embodiment, the pore size averages about 50 μm. In other embodiments, the pore size averages between about 20 μm and about 200 μm, about 20 μm and about 190 μm, about 20 μm and about 180 μm, about 20 μm and about 170 μm, about 20 μm and about 160 μm, about 20 μm and about 150 μm, about 20 μm and about 140 μm, about 20 μm and about 130 μm, about 20 μm and about 130 μm, about 20 μm and about 120 μm, about 20 μm and about 110 μm, about 20 μm and about 100 μm, about 20 μm and about 90 μm, about 20 μm and about 80 μm, about 20 μm and about 75 μm, about 20 μm and about 70 μm, about 20 μm and about 65 μm, about 20 μm and about 60 μm, about 25 μm and about 60 μm, about 30 μm and about 60 μm, about 35 μm and about 60 μm, and about 40 μm and about 60 μm. The starting melting point and the molten temperature for this particular calcium phosphate material of the invention is 885° C.

The term "appropriate reaction temperature" includes temperatures at which the phosphate and calcium ions can react and anneal, but are not molten. In a further embodiment, the appropriate reaction temperature is about 5° C. to 150° C. below the melting point of the mixture. The appropriate reaction temperature may vary based on the Ca/P ratio and may also be dependent on the calcium and phosphate ion sources.

In an embodiment, the mixture is preheated to an appropriate preheating temperature before reacting and annealing. Advantageously upon preheating, the mixture of calcium and phosphate ions form manipulable paste. The paste can then be shaped (e.g., by hand or by a mold) such that it can perform its intended function. Subsequent heating to a temperature 15° C. below its starting melting point will form a solid of the desired shape.

The term "appropriate preheating temperature" includes temperatures at which the phosphate is partially condensed and forms a manipulable paste after an appropriate length of time (e.g., about thirty minutes or a time sufficient to form a manipulable paste). In one embodiment, the appropriate preheating temperature is about 250° C.

In a further embodiment, the method also includes preheating the mixture to 400° C. to 760° C. for at least 1 second at least once, prior to the heating the mixture to the appropriate reaction temperature. The mixture may be preheated one, two, three or more times.

In another embodiment, the reaction mixture is compressed to a pressure of 10,000 psi. The reaction mixture may also be heated to 250° C. to 400° C. for an appropriate time, e.g., at least thirty minutes.

The mixture may also be molded into a shape which is advantageous for its intended purpose. For example, the reaction mixture may be placed into a mold prior to heating and pressed to a pressure of 100 psi to 20,000 psi for at least 1 second.

The mixture may be subject to ultrasonic vibration during compression. Furthermore, an acid catalyst may be added to the reaction mixture. The acid catalyst may be an inorganic or organic acid.

In a further embodiment, vacuum filtration of a salt solution and electrophoresis, may be used to remove unreacted ions and the acid catalyst from the porous solid calcium phosphate material after the reaction and annealing step.

The calcium phosphate mixtures may be heated by any appropriate method known in the art. Examples of heating mechanisms include electric furnaces, radio frequency heating, laser radiation, and microwave radiation. As used herein, the term "furnace" is used to refer to any device which is capable of heating a mixture of calcium and phosphate ions to a temperature lower than the molten state where the reactants may react.

In a further embodiment, the mixture is placed on an inert supporting material, such as boron nitride, such that reactions between the mixture and the supporting material are prevented.

The invention also pertains to a surgical implant comprising a calcium phosphate material produced by the methods of the invention. The invention also pertains to a calcium phosphate material produced by the methods of the invention.

In one further embodiment, the calcium phosphate material is produced by mixing orthophosphoric acid and hydroxyapatite and rapidly heating the mixture to 760° C., such that the mixture is dehydrated and partially condensed. The mixture is molded under high pressure and heated to an appropriate temperature (e.g., a temperature at which temperature the components react but are not molten state, e.g., 15° C. below the mixture's melting point).

In a further embodiment, the bulk density of the calcium phosphate material is manipulated by applying different pressure on the mixture in the mold before heating. The pressure applied to the mixture can vary from 100 psi to 20,000 psi. The pressure on the material constitutes a low bulk density of about 1.00 gm/cm$^3$ and the 10,000 psi pressure makes a material of bulk density about 2.2 gm/cm$^3$. In other embodiments, the calcium phosphate material of the invention has a bulk density of between about 1.0 gm/cm$^3$ to about 2.5 gm/cm$^3$, about 1.0 gm/cm$^3$ to about 2.2 gm/cm$^3$, about 1.0 gm/cm$^3$ to about 2.1 gm/cm$^3$, about 1.0 gm/cm$^3$ to about 2.0 gm/cm$^3$, about 1.0 gm/cm$^3$ to about 1.9 gm/cm$^3$, about 1.0 gm/cm$^3$ to about 1.8 gm/cm$^3$, about 1.0 gm/cm$^3$ to about 1.7 gm/cm$^3$, about 1.0 gm/cm$^3$ to about 1.6 gm/cm$^3$, about 1.0 gm/cm$^3$ to about 1.5 gm/cm$^3$, about 1.1 gm/cm$^3$ to about 2.2 gm/cm$^3$, about 1.2 gm/cm$^3$ to about 2.2 gm/cm$^3$, and about 1.3 gm/cm$^3$ to about 2.2 gm/cm$^3$.

In another embodiment, acid catalysts are used to facilitate the formation of the calcium phosphate material. Acid catalysts may be from organic or inorganic (e.g., hydrochloric acid) sources. Acid catalysts from organic sources can later be oxidized into carbon dioxide and water. Inorganic acids can be removed by water or by electrophoresis. The acid catalyst is added after the preheating stage (e.g., dehydration and partially condensing stage) but before the heating to the appropriate reaction temperature (e.g., 15° C. below the molten state). In addition, this heating process to the appropriate reaction temperature can be lengthened to make ensure that the organic acid catalyst has been oxidized to carbon dioxide and water.

The unreacted soluble reactants or soluble components of the final product can be removed by water or they can be more efficiently removed by electrophoresis. Soluble unreacted inorganic acid catalysts can dissolve in water, although trapped acid in the highly porous material may diffuse out of the calcium phosphate material slowly. A more efficient way to remove the catalysts is through the use of electrophoresis which can actively remove the ions out of the material. Unreacted soluble reactants, or unstable final components such as, for example, pyrophosphate, can also be pulled out of the material much more efficiently with electrophoresis.

The calcium phosphate materials of this invention may comprise a variety of crystalline and amorphous substances. Various types of analyses have indicated that solid calcium phosphate materials include apatite calcium phosphates, mono and dibasic calcium phosphates, pyrophosphates, metaphostates, polymetaphosphates, and orthophosphate species.

For certain uses, the porous calcium phosphate material of the invention has several significant advantages over solid calcium phosphate materials, such as sintered hydroxyapatite. For example, the porous calcium phosphate material of the invention is more biodegradable than the sintered hydroxyapatite and is therefore more suitable as a bone substitute. The osteoclasts at the site of the transplantation actively dissolve the porous calcium phosphate material. The porous calcium phosphate material is replaced by the real bone (deposited by the osteoblasts), while undergoing biodegradation. Advantageously, the degradation rate of the porous calcium phosphate material is compatible with the rate of regeneration, such that the replacement does not lose its function before total degradation. In addition, the highly interconnected porosity advantageously allows for the penetration of the osteoclasts and osteoblasts into the porous calcium phosphate material of the invention, such that the material eventually becomes living bone. Examples of porous calcium phosphate material with interconnected pores are shown in FIGS. 1b–1g.

In an embodiment, the porous calcium phosphate material of the invention is produced by mixing orthophosphoric acid and hydroxyapatite. The mixture is then dehydrated and partial condensed by rapid heating to an appropriate temperature for an appropriate length of time (e.g., a temperature of about 760° C. for 30 seconds) once or repeatedly.

In another embodiment, the invention pertains to method of producing a porous calcium phosphate material. The method includes forming a mixture of calcium ions and phosphate ions, having a calcium to phosphorus ratio of 0.1 to 1.67, adding a gas-generating material to the mixture, heating the mixture an appropriate reaction temperature, and cooling the mixture such that a solid, porous calcium phosphate material is produced. Preferably, the porous calcium phosphate material produced has interconnected pores. In a further embodiment, the appropriate reaction temperature is about 5° C. to 150° C. below the melting point of the mixture To create porosity, gas-generating material may be incorporated into the mixture of calcium and phosphate ions. The pore size of the calcium phosphate material may be determined by the size of the granules of the gas-generating material. For example, to generate a calcium phosphate material with pore sizes between about 250 µm and about 400 µm, the size of the granules of gas-generating material should also be between about 250 µm and about 400 µm.

The term "gas-generating material" includes materials that generate gas when subjected temperatures below the appropriate reaction temperature and/or at reduced pressures. Examples of gases that may be generated by the gas-generating material include, but not limited to ammonia, water, hydrogen, or carbon dioxide.

In a further embodiment, the gas-generating material generates ammonia. Examples of sources of ammonia include, but are not limited to, ammonium carbonate, ammonium bicarbonate, ammonium acetate, ammonium hydroxide, ammonium nitrates, ammonium sulfates, ammonium hydrogenphosphate, ammonium dihydrogeuphosphate, ammonium fluorophosphates, ammionium citrate, ammonium hydrogencitrate, ammonium hydrogen difluoride, ammonium hydrogen oxalate hemihydrate, ammonium halides, ammonium salts, ammonia anhydride, ammonia solutions, and combinations thereof.

In another further embodiment, the gas-generating material is generates carbon dioxide. Examples of sources of carbon dioxide include, but are not limited to, ammonium carbonate, ammonium bicarbonate, metal carbonates, nonmetal carbonates and mixtures thereof.

For example, 15% by weight of the selected ammonium bicarbonate is mixed with the mixture of calcium and phosphate ions. The mixture is then molded and placed in an electric furnace. Ammonium bicarbonate starts to decompose at roughly 60° C. The heating rate is carefully controlled, such that the decomposition of ammonium bicarbonate does not occur too vigorously and create cracks in the calcium phosphate material. For example, the heating rate may be about 0.5° C./minute and the temperature may be held at 250° C. for 12 hours. This period of time allows for the decomposition of ammonium bicarbonate before the higher temperature reactions of the calcium phosphate species.

Figure 1B:
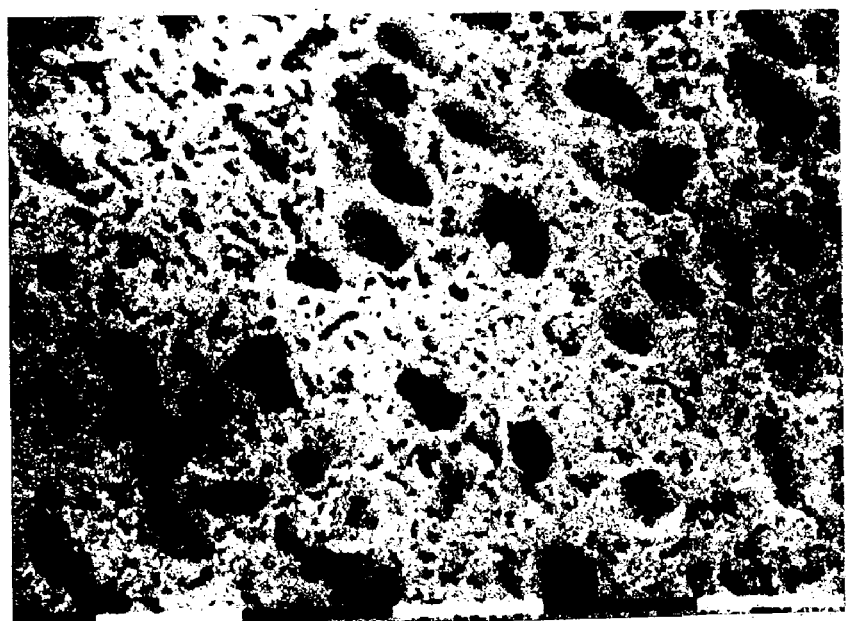
FIG. 1b is a SEM image of the calcium phosphate material with using 15% ammonium bicarbonate (particle size greater than 425 μm) at 20×magnification.
Figure 1C:
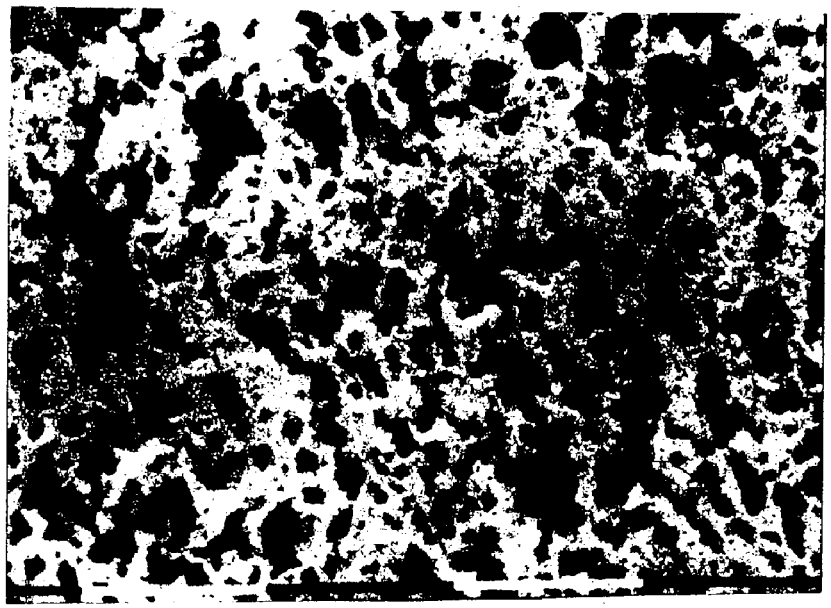
FIG. 1c is an image of the calcium phosphate material with 20% ammonium bicarbonate (particle size less than 106 μm) at a 26.4×magnification.
Figure 1D:
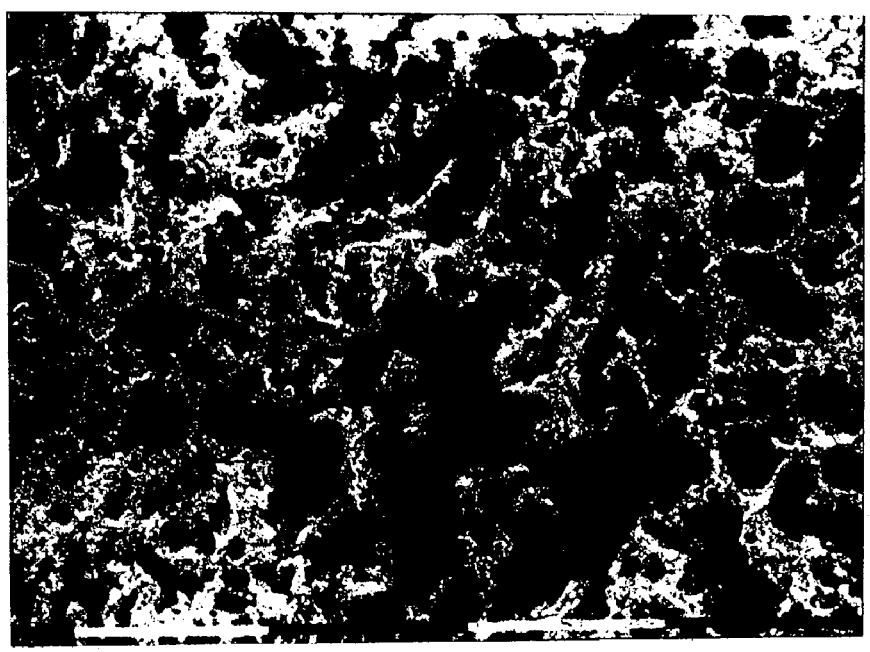
FIG. 1d is a SEM image of the calcium phosphate material with 20% ammonium bicarbonate (particle size between 212–250 μm) at a 26.4×magnification.
Figure 1E:
FIG. 1e is a SEM image of the calcium phosphate material with 20% ammonium bicarbonate (particle size between 250 and 425 μm) at a 26.4×magnification.
Figure 1F:
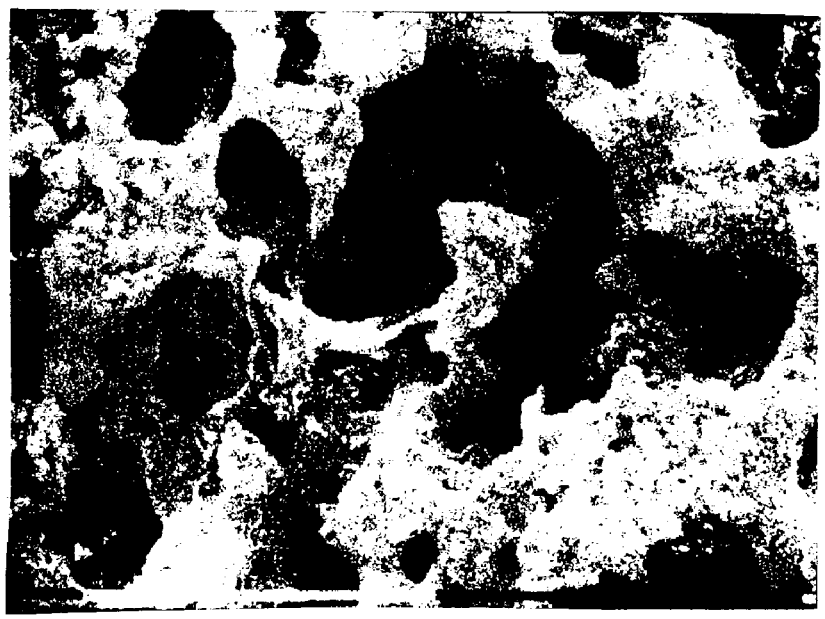
FIG. 1f is a SEM image of the calcium phosphate material with 20% ammonium bicarbonate (particle size between 250 and 425 μm) at a 50.5×magnification.
Figure 1G:
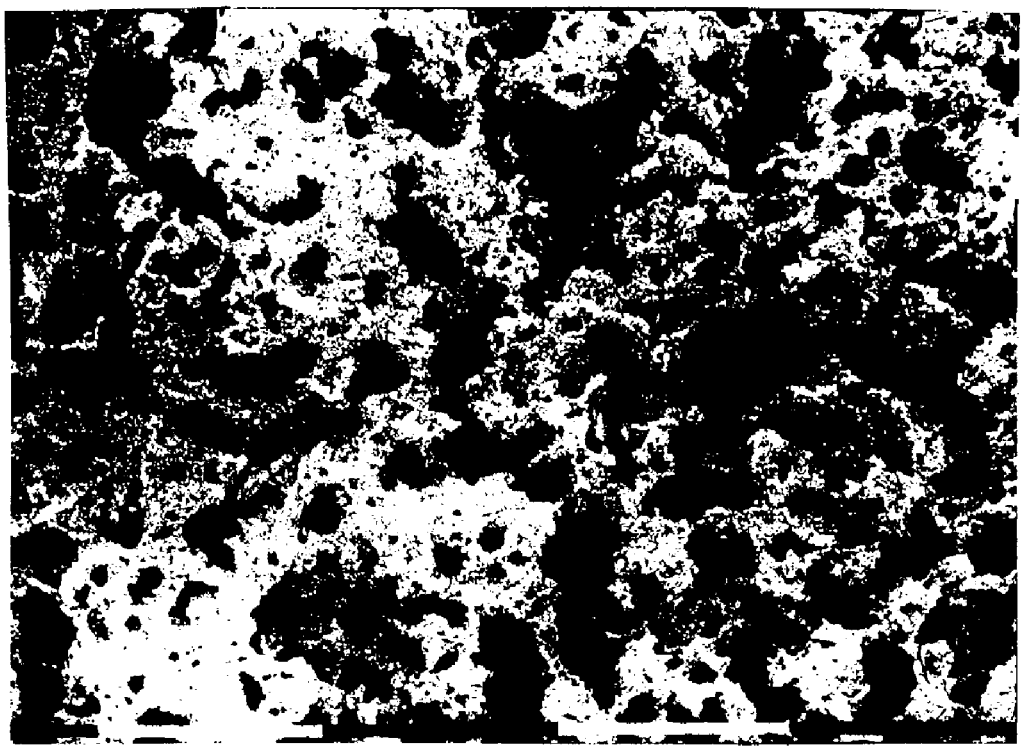
FIG. 1g is a SEM image of the calcium phosphate material with 25% ammonium bicarbonate (particle size between 125 and 250) at a 26.4×magnification.

FIGS. 1a–1g show calcium phosphate materials made with no, 15%, 20%, and 25% ammonium bicarbonate gas-generating materials (by weight, before the ammonium bicarbonate decomposed). FIG. 1a shows the control calcium phosphate material. FIG. 1b shows the calcium phosphate material using 15% ammonium bicarbonate with a particle size greater than 425 µm. FIG. 1c shows a calcium phosphate material made with 20% ammonium bicarbonate, with a particle size of less than 106 µm. FIG. 1d shows a calcium phosphate material with 20% ammonium bicarbonate with a particle size between 212–250 µm. FIG. 1e shows a calcium phosphate material made with 20% ammonium bicarbonate, with a particle size between 250 and 425 µm. FIG. 1f shows a calcium phosphate material made with 20% ammonium bicarbonate with a particle size between 250 and 425 µm. FIG. 1g shows a calcium phosphate material made with 25% ammonium bicarbonate with a particle size between 125 and 250.

Figure 2:
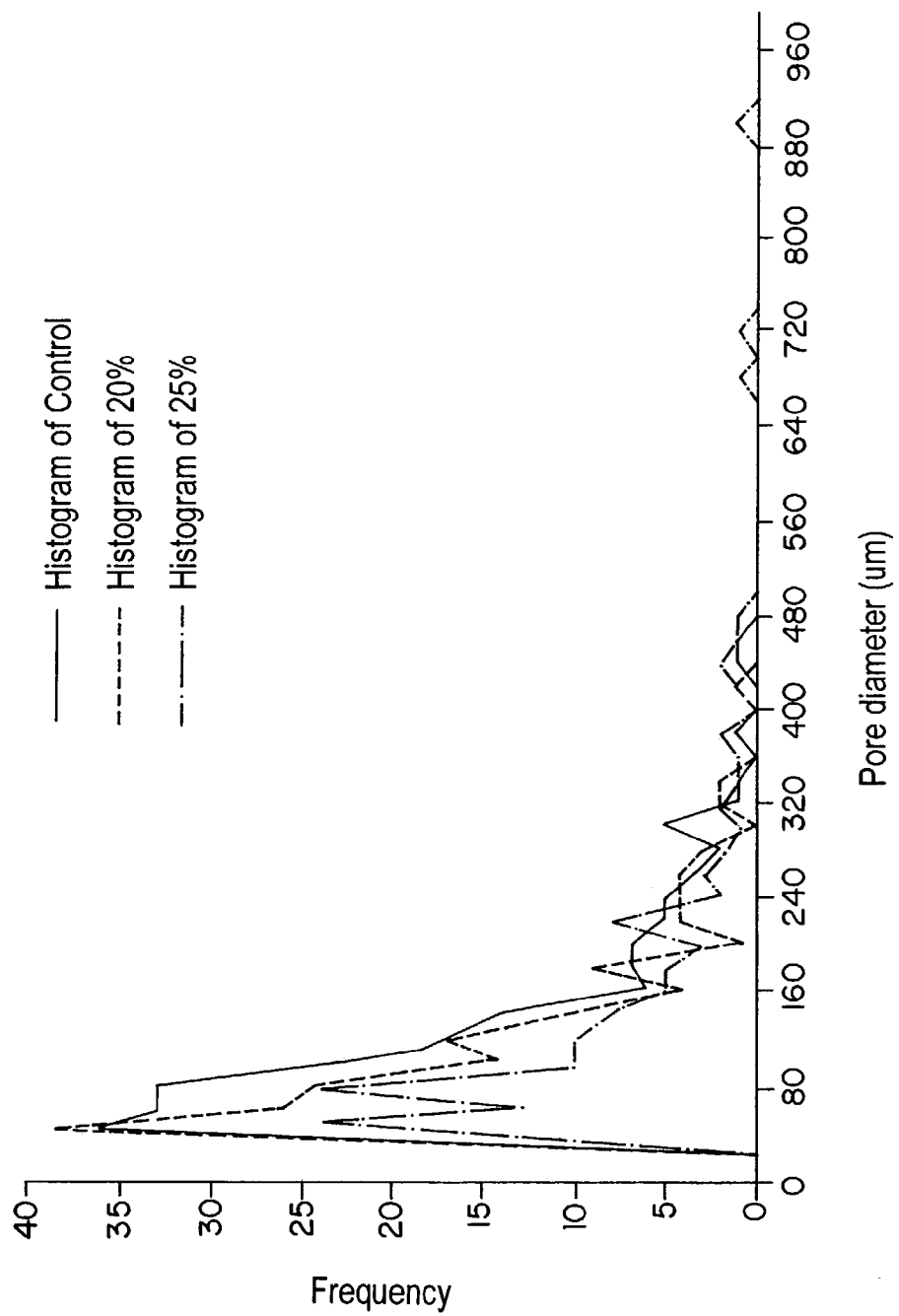
FIG. 2 is a histogram which shows the frequency of pore diameters for control calcium phosphate material (without gas-generating material), calcium phosphate made with 20% of a gas-generating material, and calcium phosphate material made with 25% of a gas-generating material.

FIG. 2 is a histogram which shows the frequency of pore diameters for control calcium phosphate material (without gas-generating material), calcium phosphate made with 20% by weight of ammonium by carbonate (with a particle size of 125–250 µm), and calcium phosphate material made with 25% by weight of ammonium carbonate with a particle size from about 106 to about 125 µm.

The subsequent heating to a higher temperature affords the energy for the reactive calcium phosphate species to react and a solid calcium phosphate ceramic material to be obtained after the heating process. The cavities left behind by the decomposition of gas generating material create interconnected pores within the calcium phosphate material. Mercury intrusion analysis shows the pore sizes have been significantly enlarged compared with the native pore sizes produced by the condensation reaction of the material. The percentage of porosity is also more then that of the material without incorporation of the gas generating material.

In another embodiment, the mixture is placed into a mold and pressed to a pressure of 100 psi to 20,000 psi for at least 1 second before being heated to the appropriate reaction temperature. In another embodiment, the mixture is subject to ultrasonic vibration bombardment while in the mold.

In another embodiment, the invention also pertains to a method of producing a porous calcium phosphate material. The method includes mixing a gas-generating material and a calcium phosphate ceramic precursor, heating the mixture to below the sintering temperature to generate a gas, and sintering the calcium phosphate ceramic precursors to make a solid material.

The term "calcium phosphate ceramic precursor" includes, for example, monocalcium phosphate hydrate (MCP), dicalcium phosphate hydrate (DCPD), dicalcium phosphate anhydrous (DCPA), octacalcium phosphate pentahydrate (OCP), tricalcium phosphate (TCP), alpha and beta from (hydroxyapatite), pentacalcium hydroxylphosphate (HAP), tetracalcium phosphate monoxide (TCPM), calcium pyrophosphate, calcium metaphospates, polycalcium metaphospates, and combinations thereof.

In another embodiment of this invention, a similar strategy can be applied to make artificial porosity by using chemicals capable of being sublimed at elevated temperature and/or reduced atmospheric pressure. For example, $H_2O$ ice can be sublimed at sub-zero ° C. temperate under vacuum, which process has been referred as freeze drying. Granules of selected sizes of ice can be mixed with mixture of reactive calcium phosphate species or calcium phosphate ceramic precursors, which is pre-chilled to sub-zero° C. The mixture can then be molded in a mod, which is also pre-chilled to sub-zero° C., the whole process would have to be conducted in a cold room of 0° C. or below to prevent melting of the ice. After the mixture has been molded, the mixture block is placed in liquid nitrogen and then a flask connected to vacuum line. After 24 hours of vacuum, the ice granules inside the block will be sublimed, leaving cavities inside the material without residues.

In an embodiment, the invention pertains to a method of producing a porous calcium phosphate material. This method comprises subliming a chemical in a reactive calcium phosphate mixture precursor, and reacting the reactive calcium phosphate mixture, to produce a porous calcium phosphate material.

In yet another embodiment, the invention also pertains at least in part to a method of producing a porous calcium phosphate material. The method includes subliming a chemical in one or more calcium phosphate ceramic precursor and sintering the calcium phosphate precursor, to produce a porous calcium phosphate material.

In a further embodiment, the chemical is selected such that it is capable of being sublimated at a temperature below 400° C. and/or at a pressure of greater than 0.1 torr.

The invention also pertains, at least in part, to interconnected porous calcium phosphate materials. The material may be generated by any method described herein. Advantageously, the material is capable of osteointegration and osteoconduction. Osteointegration can be measured as the percentage of the perimeter length of implant covered by bone, as described in the Examples. In one embodiment, the amount of osteointegration of the implant of the invention is about 5% or greater, about 10% or greater, about 11% or greater, about 12% or greater, about 13% or greater, about 14% or greater, about 15% or greater, about 16% or greater, about 17% or greater, about 18% or greater, about 19% or greater, about 20% or greater, about 21% or greater, about 22% or greater, about 23% or greater, about 24% or greater, about 25% or greater, about 30% or greater, about 35% or greater, about 40% or greater, about 45% or greater, about 50% or greater, about 55% or greater, about 60% or greater, about 65% or greater, about 70% or greater, about 75% or greater, about 80% or greater, about 85% or greater, about 90% or greater, about 95% or greater, or about 100%.

In other embodiments, the calcium phosphate material of the invention has a compression strength of about 10,000 psi or greater, about 11,000 psi or greater, about 12,000 psi or greater, about 13,000 psi or greater, about 14,000 psi or greater, about 15,000 or greater, about 16,000 psi or greater, about 17,000 psi or greater, about 18,000 psi or greater, about 19,000 psi or greater, about 20,000 psi or greater, about 21,000 psi or greater, about 22,000 psi or greater, about 23,000 psi or greater, about 24,000 psi or greater, or about 25,000 psi or greater.

In other embodiments, the calcium phosphate material of the invention has a bulk density of between about 1.0 gm/cm$^3$ to about 2.5 gm/cm$^3$, about 1.0 gm/cm$^3$ to about 2.2 gm/cm$^3$, about 1.0 gm/cm$^3$ to about 2.1 gm/cm$^3$, about 1.0 gm/cm$^3$ to about 2.0 gm/cm$^3$, about 1.0 gm/cm$^3$ to about 1.9 gm/cm$^3$, about 1.0 gm/cm$^3$ to about 1.8 gm/cm$^3$, about 1.0 gm/cm$^3$ to about 1.7 gm/cm$^3$, about 1.0 gm/cm$^3$ to about 1.6 gm/cm$^3$, about 1.0 gm/cm$^3$ to about 1.5 gm/cm$^3$, about 1.1 gm/cm$^3$ to about 2.2 gm/cm$^3$, about 1.2 gm/cm$^3$ to about 2.2 gm/cm$^3$, and about 1.3 gm/cm$^3$ to about 2.2 gm/cm$^3$.

In other embodiments, the calcium phosphate material has a porosity of between about 20% and about 80%, about 25% and about 75%, about 30% and about 70%, about 30% and about 65%, about 35% and about 65%, about 40% and about 65%, about 41% and about 65%, about 42% and about 65%, about 43% and about 65%, about 44% and about 65%, about 45% and about 65%, about 46% and about 65%, about 47% and about 65%, about 48% and about 65%, about 40% and about 64%, about 40% and about 63%, about 40% and about 62%, about 40% and about 61%, about 40% and about 60%, about 40% and about 59%, and about 40% and about 58%.

The porosity can be measured by methods known to those of skill in the art, for example, by Mercury Intrusion Porosimetry (MIP). Mercury Porosimeters deliver fast, accurate pore structure data for a wide variety of materials. They are provide an automated analysis of porous materials with pore diameters ranging from 360 to 0.0055 µm and are commericially available (Micromeritics, Norcross, Ga.).

In an embodiment, the reactive calcium phosphate mixture precursor comprises calcium phosphates, non-apatitic calcium phosphates, calcium hydroxide, calcium oxide, calcium carbonate, calcium salts, calcium halide and calcium metal, orthophosphoric acid, pyrophosphoric acids, condensed phosphates, phosphate or non-metal cations, metal phosphates, or mixtures thereof.

In an embodiment, the calcium phosphate material generated by the methods of the invention is biodegradable. In a further embodiment, the calcium phosphate material of the invention further comprises osteoinductive agents.

In a further embodiment, the calcium phosphate material comprises the calcium salt of

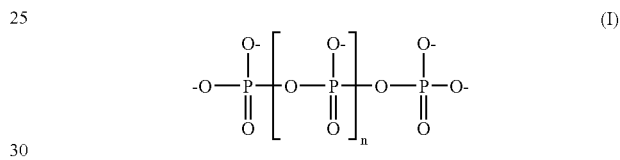

(I)

wherein n is from about 10 to about 1,000,000. In a further embodiment, n is between 50 and 1,000,000.

The term "osteoinductive agents" includes agents known in the art to enhance bone formation. Examples of such agents include, but are not limited to osteoprogenitor cells from bone morrow or bone morphogenic proteins.

In a further embodiment, the invention pertains to a method of treating a bone disorder in a subject. The method includes applying a calcium phosphate material of the invention to a bone of said subject, and allowing the bone to heal, such that the bone disorder of said subject is treated. Examples of bone disorders include fractures or other bone defects which require bone replacement. Preferably, the subject is a mammal, e.g., a sheep, dog, cat, horse, monkey, rabbit, mouse, bear, or, preferably, a human.

The methods of the present invention produce controllable porosity within a biodegradable calcium phosphate material which is suitable for certain applications where high porosity is favored. The higher porosity has been reported to be beneficial for the infiltration of osteoclasts and osteoblasts into the ceramic material, and which facilities the turn over rate of the biodegradable ceramic that closely resembles the real bone.

Those skilled in the art will recognize, or be able to ascertain using no more than routine experimentation, many equivalents to the specific embodiments and methods described herein. Such equivalents are intended to be encompassed by the scope of the following claims. All patents, patent applications, and literature references cited herein are hereby expressly incorporated by reference.

EXEMPLIFICATION OF THE INVENTION

The invention is further illustrated by the following examples which should not be construed as limiting.

EXAMPLE 1

30 gm of hydroxyapatite (from Mutter Chemical Company under the name of tricalcium phosphate, $Ca_{10}(PO_4)_6(OH)_2$) was added to 32.5 ml of 85% orthophosphoric acid in a porcelain bowl. The mixture was ground and heated at 760° C. for 30 seconds. This process was repeated twice. The mixture was cooled down and placed in a stainless mold. A hydraulic press was used to compress the powder mixture in the mold to about 10,000 psi for about 30 seconds and then removed from the mold. The pressed mixture was then heated in an electric furnace on an inert boron nitride support. The heating rate was about +1.67° C./minute and the temperature was held at 870° C. (e.g., 20° C. below 890° C., the beginning of the molten state of the reacting mixture) for 12 hours. After the 12 hours' incubation, the calcium phosphate block was cooled down slowly at the rate of −1.67° C./minute to room temperature.

Qualitative analysis of the block showed that the calcium phosphate material contained 19.65% calcium, 30.75% phosphorus, less than 0.1% nitrogen and less then 0.1% hydrogen. The infrared spectrum signature indicated the existence of polymetaphospate in the solid and powder X-ray diffraction showed a mixture of other calcium phosphate species.

The bulk density of the material was about 1.46 cm/cm$^3$. The apparent density was about 300 gm/cm$^3$. The compression strength of the mixture was about 20,000 psi. The porosity of the material was determined to be around 50% with an average pore size of 50 μm, and the surface area is about 0.019 m2/g. Vacuum infiltration with polymethacrylate and subsequent removal of the calcium phosphate material with hydrofluoric acid created a negative representation of the porosity showing highly interconnectivity of the pores inside the material. The calcium to phosphorus ratio of this material was around 0.486.

EXAMPLE 2

30 gm of hydroxyapatite (from Mutchler Chemical, $Ca_{10}(PO_4)_6(OH)_2$) is added to 32.5 ml of 85% orthophosphoric acid in a porcelain bowl. The mixture is ground and heated at 760° C. for 30 seconds and this process is repeated twice, before being cooled to room temperature. The mixture is pressed under 10,000 psi for about 30 seconds. Then the mixture is heated in an electric furnace at a rate of 0.5° C./minute and the temperature is held at 250° C. for 30 minutes. After the 30 minutes' incubation, the temperature is cooled down to room temperature. The resulting mixture is a manipulable white-colored paste and which can be shaped with hand or placed in a mold. Then, the shaped paste is placed on an inert boron nitride surface in an electric furnace and the temperature is raised at the rate of 1.67° C./minute to 870° C. (e.g., 20° C. below the beginning of the molten state of the reacting mixture). The temperature is then held at 870° C. for another 12 hours. At the end of the 870° C. incubation, the temperature is gradually reduced to room temperature at a rate of 1.67° C./minute.

Qualitative analysis of the block shows the calcium phosphate material contains 19.65% calcium, 30.75% phosphorus, less than 0.1% nitrogen and less then 0.1% hydrogen. Infrared spectrum signature indicates the existence of polymetaphospate in the solid and powder X-ray diffraction also shows a mixture of other calcium phosphate species in the composition.

The bulk density of this material is about 1.46 cm/cm$^3$. The apparent density is about 3.00 gm/cm$^3$. The compression strength of the mixture is about 20,000 psi. Mercury intrusion shows the porosity of the material is about 50%, with an average pore size 50 μm. The mercury intrusion also shows that the surface area of the material is about 0.019 m$^2$/g. Vacuum infiltration with polymethacrylate and subsequent removal of the calcium phosphate material with hydrofluoric acid creates a negative representation of the porosity showing highly interconnectivity of the pores inside the material. The calcium to phosphorus ratio of this material is around 0.486.

EXAMPLE 3

Using the method described in Example 1, the pressure applied to the mixture while being placed in a stainless mold is varied. The pressure applied to the mold ranged from about 100 psi to 20,000 psi. The volume of the resulting mixture varies corresponding to the applied pressure. After the subsequent heating in the furnace according to the same procedure described in Example 1, the bulk density of the pressured mixture ranged from around 1.0 gm/cm$^3$ to 2.2 gm/cm$^3$.

EXAMPLE 4

30 gm of hydroxyapatite (from Mutchler Chemical Company under the name of tricalcium phosphate, $Ca_{10}(PO_4)_6(OH)_2$) is added to 32.5 ml of 85% orthophosphoric acid in a porcelain bowl. The mixture is ground and heated at 760° C. for 30 seconds three times. The mixture is cooled down and 1 ml of 0.1M HCl is added to the mixture and the resulting mixture is heated to 200° C. for five minutes. The resulting mixture is then placed in stainless mold. A hydraulic press is used to compress the powder mixture in to the mold to about 10,000 psi for about 30 seconds. While pressing the mixture in the mold, a source of ultrasound, such as a ultrasound probe, may be applied on the stainless mold to help packing the mixture inside the mold. The block of mixture is then removed from the mold. The pressed mixture is then heated in an electric furnace sitting on an inert boron nitride supporting material. The heating rate is about +1.67° C./minute and the temperature is held at 870° C. (e.g., 20° C. below 890° C., the beginning of the molten state of the reacting mixture) for 12 hours. After the 12 hours' incubation, the reacted calcium phosphate block is cooled down slowly at the rate of −1.67° C./minute to room temperature. The acid is later removed by electrophoresis described in Example 2.

EXAMPLE 5

With the same procedure described in either Example 1 or 3, after the mixture has been heated under 870° C. for 12 hours, the mixture is cooled down and then placed in a vacuum flask, which is connected to a vacuum line. The atmospheric pressure inside the flask is then reduced to 25 microns of mercury. 0.1 NaCl is then injected into the flask and the material is totally submerged in the salt solution. The material is then placed in a electrophoresis cell and 150 volts of voltage is applied to the cell for 30 minutes. The material is then rinsed out in 1 gallon of distilled water twice to remove the salt solution.

EXAMPLE 6

30 gm of hydroxyapatite (from Mutchler Chemical Co., $Ca_{10}(PO_4)_6(OH)_2$) is added to 32.5 ml of 85% orthophosphoric acid in a porcelain bowl. The mixture is ground and heated at 760° C. for 30 seconds three times. The mixture is cooled down to room temperature. Particles of ammonium bicarbonate are selected by sieves of pore sizes between 250 μm and 400 μm. 1.5 parts by weight of the ammonium bicarbonate of selected particle sizes are mixed with 8.5 parts of the calcium phosphate mixture. This mixture is pressed under 10,000 psi for 30 seconds and then heated in an electric furnace. The heating rate is 0.5° C./minute and the temperature is held at 250° C. for 12 hours. After the 12 hours' incubation the temperature is raised at the rate of 1.67° C./minute of 870° C., 20° C. below the beginning of the molten state of the reacting mixture, and the temperature stays at 870° C. for another 12 hours. At the end of 870° C. incubation, the temperature is gradually cooled down to room temperature at the rate of 1.67° C./minute.

The bulk density of this material is about 1.3 gm/cm$^3$. The apparent density is about 3.10 gm/cm$^3$. The compression strength of the mixture is about 11,000 psi. Mercury intrusion shows the its porosity is around 58%, with average pore size 130 μm. Vacuum infiltration with polymethacrylate and subsequent removal of the calcium phosphate material with hydrofluoric acid creates a negative representation of the porosity showing highly interconnectivity of the pores inside the material.

EXAMPLE 7

Using apatitic or non-apatitic calcium phosphate ceramic precursors to make sintered form of solid material, these precursors can be mixed with certain weight percentage of ammonium bicarbonate to create controlled porosity of desired sizes. The weight percentage can be varied according to the need. A 15 parts of selected pore sizes of solid ammonium bicarbonate are mixed with 85 parts of alpha form tricalcium phosphate. The mixture is then pressed to make solid block. This block is then placed in an electric furnace and the temperate is raise slowly at the rate of 0.5° C./minute to 250° C. and stays at 250° C. for 12 hours. After the 12 hours incubation, the temperature of the furnace is raised to the sintering temperature of the alpha tricalcium phosphate.

EXAMPLE 8

To control porosity using chemicals capable of sublimation alpha form tricalcium phosphate, or other calcium phosphate ceramic precursors, can be mixed with certain weight percentage of water ice at −20° C. to create controlled porosity of desired sizes. The alpha form tricalcium phosphate ceramic precursor needs to be pre-chilled in a cold room at 0° C. or below. The weight percentage can be varied according to the need. A 15 parts of selected pore sizes of solid water ice are mixed with 85 parts of alpha form tricalcium phosphate. The mixture is then pressed in a pre-chilled mold below 0° C. to make solid block of the ceramic precursor. This block is then placed in liquid nitrogen and subsequently in a container connected to a freeze drying apparatus. The temperature is left to raise slowly as the vacuum at 200 micron Mercury is applied to the material. After the 24 hours incubation, the dehydrated material is then placed in an electric furnace and the temperature of the furnace is raised to the sintering temperature of the furnace is raised to the sintering temperature of the alpha tricalciumn phosphate.

EXAMPLE 9

This example shows the use of the calcium phosphate material for spinal fusion in sheep.

Posterior spinal fusions are commonly performed for a wide variety of disorders including deformities, tumors and fractures. Large quantities of bone graft are often necessary. The standard procedure is to harvests autologous bone graft from the iliac crest. This technique carries a significant morbidity and complication rate, often involving a second incision with the attendant risks of bleeding, infection and persistent donor site pain. Furthermore, adequate graft may not be always obtainable, especially following previous spinal operations, in osteoporotic patients with poor bone stock or treating patients with metastatic tumor.

Allograft bone has been used as an alternative. Allografts may not be as readily available, are not as effective as a posterior onlay substance, are costly to procure and have the potential for disease transmission. Due to these shortcomings, researchers have attempted to develop a bone graft substitute. The ideal synthetic bone replacement would be mechanically comparable in strength to autologous bone, be easily fashioned for implantation and possess the ability to be biologically incorporate. Implant materials composed of calcium phosphate are probably the most biocompatible synthetic hard tissue implant materials presently available. These ceramics are available as hydroxyapatite, tricalcium phosphates, or combinations of the two (porous, nonporous implants or granular particles) Tricalcium phosphate is porous and rapidly degraded. It is also mechanically weaker than hydroxyapotite. Replamine form hydroxyapatite is formed by a hydrothermal exchange process using coral (porites) as a porous calcium carbonate skeleton. Limitations include incorporate conversion of the carbonate, variable sizes and shapes of the original coral exo-skeleton and this material is also structurally weak compared to biological bone.

MATERIALS AND METHODS

Implant Description

Highly porous calcium polyphosphate material with a calcium phosphate ratio of 0.55 was fabricated from this animal study in match stick shapes. Pore diameter ranged up to 200 microns. The material was sterilized using radiation techniques.

OPERATIVE TECHNIQUE 12 conditioned adult male sheep were used in this example. After general endotracheal anesthesia, each animal was placed prone on the operating table, prepped and draped in sterile fashion. Two midline longitudinal incisions were made. An incision between L1–2 was carried down to the spinous process. The midline spinous process and ligaments were preserved and the dissection was carried laterally out to the tips of the transverse process, between L1 and L2. Decortication and facetectomy was accomplished using gauges and curettes. In similar fashion, a separate incision was made at the L4–5 location and dissection carried down to the tips of the transverso process of L4 and 15 bilaterally and similar decortication and facetectomy accomplished. Cortical cancerous bone graft was harvested from both iliac crests in two separate incisions, using ostotomics and curettes. This autologous bone graft was then fashioned into small bony strips and bone graft was then implanted at the L1–2 level, bone graft being placed bilaterally in symmetrical fashion between the transverse processes of L1 and L2. A similar quantity and size of calcium phosphate bioceramic was placed between the transverse processes of the L4–5 lumbar segment in similar fashion. Furthermore, calcium phosphate bioceramic match stick material was used to fill the void created over the left iliac crest which was then closed in standard fashion with vinyl sutures in layers. The right iliac crest donor site was closed leaving the iliac crest donor site void unfilled. The midline incisions were closed in similar fashion. The procedure was repeated for the other animals using alternate levels L1–2 vs. L4–5. (Calcium polyphosphate graft placed at L1–2 and autologous bone at L4–5.)

The animals were housed in the intensive care unit in individual pens. Prophylactic antibiotics were administered for 24 hours. The sheep were allowed to weight bear immediately. Postoperative analgesia was administered consisting of Bupernorphine 0.005 mg to kg q. 4–6 hours for pain. The animals were killed after six months by barbiturate overdose. The lumbar spine motion segments and iliac crests were harvested and cleaned of all soft tissues.

MANUAL PALPATION

At the time of harvest, the lumbar spines were manually palpated at the level of the fused motion segment, compared to the levels of the adjacent motion segments proximal and distal. This simulated fusion exploration and palpation in humans is considered the gold standard for distinguishing nonunions and solid fusions. These motion segments were graded as solid or not solid. Only levels grades as solid were considered to be fused.

RADIOGRAPHIC ANALYSIS

Posterior/anterior radiographs were made and multiplane CT scans were then performed of all motion segments. These radiographs were then reviewed and the fusions were graded as solid or not solid based on the presence of continuous trabeculac within the intertransverse fusion mass.

BIOMECHANICAL TESTING

Nondestructive cyclic testing was performed with an 8 by 8 bionic hydraulic material testing machine (materials testing systems, Minneapolis, Minn.) on four axis, (flexion, extension, right lateral bending and left lateral bending). A ramp made in the shape of a triangle wave of 0.1 hertz was applied ten times, data was taken during the last cycle. Testing was performed using a 4 point bending model, intervertebral displacement was measured by an extensometer mounted anteriorly across the disc space at the level of fusion. Additionally, lumbar motion segments from sheep of similar size, age and weight were compared as a control group.

LIGHT MICROSCOPIC ANALYSIS

The harvested spine specimens and iliac crest were fixed in 10% formalin. They were cut in half longitudinally in the sagittal plane and sagittal sections were sections were prepared. Undecalcified sections were dehydrated, infiltrated and imbedded in technovit based methylmethacrylate. Using a water cooled diamond saw, sections approximately 150–200 microns in thickness were prepared. These were hand ground to approximately a thickness of 320 microns using silicon cartridge paper immersed in water and stained using a modified McNeals (tetrachrome stain). Sections were submitted from back scatter electron microscopy. This technique was used to analyze the volume fraction of soft tissue, bone, implant and osteointegration (percentage of the perimeter length of implant covered by bone) and compare the relative amounts of soft tissue and calcified matrix in the sections.

RESULTS

Mortality and Complications

All sheep tolerated the surgical procedure well, they were ambulating and gaining weight postoperatively. No infections occurred. One animal was euthanized at one week postoperatively due to uncontrollable pain probably from the iliac crest donor site. There was no neurological deficit noted. One other animal dies six weeks after surgery by an unrelated accident. The pre-operative morbidity rate was 16% (two deaths out of twelve sheep).

Gross Inspection/Palpation/Radiographs

Manual palpation of the fused and adjacent unfused segments were performed in all animals at the time of harvest. The fusion masses appeared larger in the calcium polyphosphate bioceramic levels compared to the autologous grafted segments. The average volume being approximately 72 cm$^3$ vs. 43 cm$^3$, that is difference of 29.6 cm$^3$ which is significant (P value 0.0145). A fibrous membrane appeared to encapsulate the fusion masses more noticeable on the calcium polyphosphate bioceramic fused segments compared to the autologous grafted segments. There was no evidence of gross inflammation. One of the spines developed a nonunion at both the autologous bone grafted level and at the calcium polyphosphate bioceramic grafted level. On direct inspection and palpation, one other nonunion was noted at a calcium polyphosphate bioceramic level. All of the remaining seventeen motion segments appeared to be successfully fused.

Radiographs confirmed bony trabeculation crossing the fusion mass in all the unions. CT scans demonstrated incorporation of the bioceramic match sticks into the fusion mass. The ceramic material lying further away from the bony surface of the lamina appeared to have more soft tissue interposition and variable bony ingrowth. The CT scans also confirmed the size of the fusion masses being larger in the bioceramic levels when compared to autologous levels.

BIOMECHANICAL TESTING

The slopes of the force vs. displacement and the force vs. strain curves were calculated for each of the spine fusion segments analyzed. More variation appeared to occur in the slope of the force vs. strain data reflecting probable variations in the connection of the extensometer used to measure strain. Good results were seen with the force vs. displacement data reflecting direct measurement of the load site displacement in the MTF fixture during the spine testing. Comparing the upper (L1–2) and the lower (L4–5) fusion segments showed no statistical significant difference. The slope data was also analyzed to determine if the autologous and bioceramic fusion segments were comparable. Again, there was no statistical significant difference between the two. Both the autologous and bioceramic spines had higher slopes when compared with the unfused controlled segments in all bending modes tested. All of these variations were statistically significant (p, 0.05). One of the autologous and two of the bioceramic spinal segments appeared to be notiunions showing very low values for the slope of the force vs. displacement curve in all four bending modes. This reconfirmed the findings on direct manual palpation.

Light Microscopy and Backscatter Electron Microscopy Dystrometry

A dense collagenenous connective tissue with vascular capsule was encountered on the surface of the fusion masses using the calcium polyphosphate bioceramic. There was no evidence of an inflammatory response nor resorption of the ceramic. Tremendous woven bone and osteoid was seen permeating between the ceramic material. Furthermore, proteinaceous material was seen within the ceramic pores of the material itself. The SEM backscatter studies confirmed ingrowth of woven bone into the porous implant matrix. The average new bone seen was 35.47%. The degree of osteo integration was also calculated by this method and determined to be on average 14.47%.

The model used in this example is similar to the posterolateral intertransverse fusion model used in humans. Two separate incisions were utilized avoiding the risk of contamination between the two levels and diminishing the amount of soft tissue stripping that occurred. Furthermore, no internal fixation was utilized. The calcium polyphosphate material graft was used on its own without osteo inductive agents such as bone marrow, bone morphogenic proteins or electrical stimulation. In this regard, the results of this example are better than one might expect when one considers the challenging environment imposed on the artificial graft material. It is known that when using ceramics, it is critical to have direct apposition of the material to the host bone, that the host bone is viable and that the interface between the implant and the artificial bone by stabilized avoiding macro motion. As mentioned, this example did not use internal fixation and therefore rigid fixation was not accomplished and yet acceptable fusion levels did occur. The calcium polyphosphate bioceramics is an osteo-conductive agent and a scaffolding for bony ingrowth. The CT scan studies and histology studies confirmed that more bony ingrowth occurred near the surface between the implant and the underlying host lamina bone, while more soft tissue ingrowth was seen between the ceramic strips lying further away from the host bone as described by Booker. When one considers this challenging environment, the nonunion rate of three out of 20 segments fused is an acceptable range (compared to human clinical studies). It is of interest that two of the nonunions occurred in the same animal at an autologous level and at the bioceramic level.

The histological results confirmed bony ingrowth between and into the artificial material. The backscatter electron studies confirm ingrowth to be an average of 35.47%, which is comparable to other studies. The biomechanical studies confirmed the strength of the fusion masses to be comparable between the artificial bone and the autologous bone levels. It is possible, though, that more remodeling occurred at the autologous fusion segment leveis compared to the calcium polyphosphate bioceramic levels as no evidence of resorption of the ceramic was noted and the average size of the fusion mass appeared larger in the artificial bone level compared to the autologous level, a difference of approximately 29.6 cm$^3$. The ceramic has been noted to slowly resorb with time and it would be of interest to assess this implant material over a longer period.

The calcium polyphosphate material is noted to be much harder than other ceramics currently available and felt to posses strength comparable to autologous bone. The advantage of the calcium phosphate material of the invention is more likely to be noted when used as a structurally supportive material in situations under compression such as anterior spinal column reconstructions.

In conclusion, this example shows that a fusion mass can be successfully created with the calcium polyphosphate material of the invention as an osteo-conductive scaffold for new bone ingrowth. Furthermore, the fusion masses are mechanically comparable to the autologous levels. Both the riographic and histolotic evidence of bony ingrowth occurred and are comparable to other studies using artificial bone implants. No soft tissue inflammatory reaction occurred.

The invention claimed is:

1. A method of producing a porous calcium phosphate material; composing:
   forming a mixture of calcium ions and phosphate ions having a calcium to phosphorus ratio of between 0.1 and about 0.80;
   heating said mixture to temperature of about 5° C. to 150° C. below the melting point of the mixture; and
   cooling the reaction mixture, such that a porous calcium phosphate material is produced.

2. The method of claim 1, further comprising preheating said mixture to 400° C. to 760° C. for at least 1 second.

3. The method of claim 2, wherein said mixture is preheated to 400° C. to 760° C. for at least 1 second two or more times.

4. The method of claim 1, further comprising compressing said mixture to a pressure of 10,000 psi.

5. The method of claim 1, wherein said ratio of calcium to phosphate ions is about 0.40 to about 0.60.

6. The method of claim 4, further comprising heating said mixture at 250° C. to 400° C. for at least thirty minutes.

7. The method of claim 1, further comprising placing the mixture into a mold prior to heating and pressing the mixture to a pressure of 100 psi to 20,000 psi for at least 1 second.

8. The method of claim 7, further comprising ultrasonic vibration bombardment of said mixture.

9. The method of claim 1, further comprising adding an acid catalyst to said mixture.

10. The method of claim 9, wherein said acid catalyst is an inorganic or organic acid.

11. The method of claim 1, wherein said calcium ions are from apatitic calcium phosphates, non-apatitic calcium phosphates, calcium hydroxide, calcium oxide, calcium carbonate, calcium salts, calcium halide, calcium metal, or combinations thereof.

12. The method of claim 1, wherein said phosphate ions are from orthophosphoric acid, pyrophosphoric acids, condensed phosphates, phosphate of non-metal cations, metal phosphates, or combinations thereof.

13. The method of claim 1, wherein said mixture is heated by an electric furnace, laser radiation, microwave radiation or radio frequency heating.

14. A method of producing a porous calcium phosphate material comprising: forming a mixture of calcium ions and phosphate ions, wherein the ratio of calcium ions to phosphorous ions is between 0.1 and about 0.80; adding a gas-generating material to said mixture; heating said mixture to about 5° C. to 150° C. below the melting point of the mixture; and cooling said mixture such that a solid, porous calcium phosphate material, is produced.

15. The method of claim 14, wherein said gas-generating material is a source of ammonium ions selected from the group consisting of ammonium carbonate, ammonium bicarbonate, ammonium acetate, ammonium hydroxide, ammonium nitrates, ammonium sulfates, ammonium hydrogen phosphate, ammonium dihydrogenphosphate, ammonium fluorophosphates, ammonium citrate, ammonium hydrogencitrate, ammonium hydrogen difluoride, ammonium hydrogen oxalate hemihydrate, ammonium halides, ammonium salts, ammonia anhydride, ammonia solutions, and combinations thereof.

16. A method of producing a porous non-apatatic calcium phosphate material comprising: mixing a gas-generating material and a calcium phosphate ceramic precursor, heating said mixture to below the sintering temperature to generate a gas; and sintering the calcium phosphate ceramic precursors to make solid ceramic materials, such that a porous non-apatitic calcium phosphate material is produced.

17. The method of claim 16, wherein said calcium phosphate ceramic precursor is monocalcium phosphate hydrate (MCP), dicalcium phosphate hydrate (DCPD), dicalcium phosphate anhydrous (DCPA), octacalcium phosphate pentahydrate (OCP), tricalcium phosphate (TCP), alpha and beta form (hydroxyapatite), pentacalcium hydroxylphosphate (HAP), tetracalcium phosphate monoxide (TCPM), calcium pyrophosphate, calcium metaphospates, polycalcium metaphospates, or combinations thereof.

* * * * *